(12) United States Patent
Han et al.

(10) Patent No.: US 6,180,761 B1
(45) Date of Patent: Jan. 30, 2001

(54) CASEIN FROM KOREAN CATTLE

(75) Inventors: Sang Kee Han, 123-1201, Kwanakhyundai Apartment, 1, Bongchun-dong, Kwanak-ku Seoul 151-050; Yoo Cheol Shin, Seoul, both of (KR)

(73) Assignee: Sang Kee Han, Seoul (KR)

( * ) Notice: Under 35 U.S.C. 154(b), the term of this patent shall be extended for 0 days.

(21) Appl. No.: 09/269,220

(22) PCT Filed: Sep. 23, 1997

(86) PCT No.: PCT/KR97/00182

§ 371 Date: Mar. 23, 1999

§ 102(e) Date: Mar. 23, 1999

(87) PCT Pub. No.: WO98/12222

PCT Pub. Date: Mar. 26, 1998

(30) Foreign Application Priority Data

Sep. 23, 1996 (KR) .................................................. 96/43482

(51) Int. Cl.⁷ ...................................................... C07K 1/00
(52) U.S. Cl. ............................................. 530/360; 530/350
(58) Field of Search ..................................... 530/360, 350

(56) References Cited

U.S. PATENT DOCUMENTS 5,739,407 * 4/1998 Bergstrom et al. ...................... 800/2
5,834,427 * 11/1998 Han et al. ............................... 514/12
5,843,705 * 12/1998 Di'Tullio et al. ..................... 435/69.1

* cited by examiner

Primary Examiner—Deborah Crouch
(74) Attorney, Agent, or Firm—Staas & Halsey LLP (57) ABSTRACT

A new casein is disclosed isolated from the milk of Korean cattle with a β-casein A¹H genotype. Amino acid sequence analysis of the casein revealed a length of 209 amino acids, where, in comparison to the more conventional β-casein variant A², at amino acid position 25, Arg is replaced by Cys, at position 88, Leu is replaced by Ile, at position 117, Gln is replaced by Glu, at position 175, Glu is replaced by Gln, and at position 195, Gln is replaced by Glu. The new casein variant disclosed can be mass produced by the selective breeding of individual bovines to produce large quantities of milk containing the new casein variant. In one example of such breeding, a female calf was born that subsequently produced the inventive casein at a yield of 4.5 kg per day. The new casein gene can be detected DNA hybridization analysis in bovines secreting the new casein. The new casein increases the absorption of casein from the small intestine about 5% in the upper region of the small intestine and about 20% in the lower region of the small intestine. Thus, this new casein can be formulated in to foodstuffs, such as infant formula, dairy products, and to treat diseases, such as osteoporosis and anemia. Further, the new casein can also be formulated into skin and hair products.

1 Claim, 3 Drawing Sheets

```
                           SEQUENCE LISTING

<160> NUMBER OF SEQ ID NOS:  7

<210> SEQ ID NO 1
    <211> LENGTH: 209
    <212> TYPE: PRT
    <213> ORGANISM: Bos taurus
    <220> FEATURE:
    <221> NAME/KEY: ACT_SITE
    <222> LOCATION: (15)
    <223> OTHER INFORMATION: pospholyated serine
    <221> NAME/KEY: ACT_SITE
    <222> LOCATION: (17)..(19)

<400> SEQUENCE: 1

Arg Glu Leu Glu Glu Leu Asn Val Pro Gly Glu Ile Val Glu Ser Leu
     1               5                  10                  15

Ser Ser Ser Glu Glu Ser Ile Thr Cys Ile Asn Lys Lys Ile Glu Lys
                20                  25                  30

Phe Gln Ser Glu Glu Gln Gln Gln Thr Glu Asp Glu Leu Gln Asp Lys
                35                  40                  45

Ile His Pro Phe Ala Gln Thr Gln Ser Leu Val Tyr Pro Phe Pro Gly
            50                  55                  60

Pro Ile Pro Asp Ser Leu Pro Gln Asn Ile Pro Pro Leu Thr Gln Thr
     65                  70                  75                  80

Pro Val Val Val Pro Pro Phe Ile Gln Pro Glu Val Met Gly Val Ser
                    85                  90                  95

Lys Val Lys Glu Ala Met Ala Pro Lys His Lys Glu Met Pro Phe Pro
                100                 105                 110

Lys Tyr Pro Val Glu Pro Phe Thr Glu Ser Gln Ser Leu Thr Leu Thr
                115                 120                 125

Asp Val Glu Asp Leu His Leu Pro Pro Leu Leu Leu Gln Ser Trp Met
            130                 135                 140

His Gln Pro His Gln Pro Leu Pro Pro Thr Val Met Phe Pro Pro Gln
    145                 150                 155                 160

Ser Val Leu Ser Leu Ser Gln Ser Lys Val Leu Pro Val Pro Gln Lys
                    165                 170                 175

Ala Val Pro Tyr Pro Gln Arg Asp Met Pro Ile Gln Ala Phe Leu Leu
                180                 185                 190

Tyr Gln Glu Pro Val Leu Gly Pro Val Arg Gly Pro Phe Pro Ile Ile
                195                 200                 205

Val

<210> SEQ ID NO 2
    <211> LENGTH: 209
    <212> TYPE: PRT
    <213> ORGANISM: Bos taurus

<400> SEQUENCE: 2

Arg Glu Leu Glu Glu Leu Asn Val Pro Gly Glu Ile Val Glu Ser Leu
     1               5                  10                  15

Ser Ser Ser Glu Glu Ser Ile Thr Arg Ile Asn Lys Lys Ile Glu Lys
                20                  25                  30

Phe Gln Ser Glu Glu Gln Gln Gln Thr Glu Asp Glu Leu Gln Asp Lys
```

-continued

```
                35                  40                  45
Ile His Pro Phe Ala Gln Thr Gln Ser Leu Val Tyr Pro Phe Pro Gly
 50                  55                  60

Pro Ile Pro Asp Ser Leu Pro Gln Asn Ile Pro Pro Leu Thr Gln Thr
 65                  70                  75                  80

Pro Val Val Pro Pro Phe Leu Gln Pro Glu Val Met Gly Val Ser
                 85                  90                  95

Lys Val Lys Glu Ala Met Ala Pro Lys His Lys Glu Met Pro Phe Pro
                100                 105                 110

Lys Tyr Pro Val Gln Pro Phe Thr Glu Ser Gln Ser Leu Thr Leu Thr
                115                 120                 125

Asp Val Glu Asp Leu His Leu Pro Pro Leu Leu Gln Ser Trp Met
130                 135                 140

His Gln Pro His Gln Pro Leu Pro Pro Thr Val Met Phe Pro Pro Gln
145                 150                 155                 160

Ser Val Leu Ser Leu Ser Gln Ser Lys Val Leu Pro Val Pro Glu Lys
                165                 170                 175

Ala Val Pro Tyr Pro Gln Arg Asp Met Pro Ile Gln Ala Phe Leu Leu
                180                 185                 190

Tyr Gln Gln Pro Val Leu Gly Pro Val Arg Gly Pro Phe Pro Ile Ile
                195                 200                 205

Val
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer 5'
      for DNA amplification

<400> SEQUENCE: 3
caacagcctt attcagaaga gtgg                                          24

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer 3'
      for DNA amplification

<400> SEQUENCE: 4
cagtgggatg acagaaagta gtcgtatagg                                    30

<210> SEQ ID NO 5
<211> LENGTH: 194
<212> TYPE: DNA
<213> ORGANISM: Artificial Sequence
<220> FEATURE:
<223> OTHER INFORMATION: Description of Artificial Sequence: Amplified
      DNA sequence

<400> SEQUENCE: 5
ttttttaaag ctagacctga ttttattttt attttccaa aggaatctat tacatgcatc     60
aataaggtaa aacccctcat atttaaatgt acattttttt aaatttcatg tttgattttt   120
ataaacagca tttatttatg tattttttt taaccagaa aattgagaag tttcagagtg    180
aggaacagca gcaa                                                    194

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: exon 5

<400> SEQUENCE: 6

Glu Ser Ile Thr Cys Ile Asn Lys
  1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: exon 6

<400> SEQUENCE: 7

Lys Ile Glu Lys Phe Gln Ser Glu Glu Gln Gln Gln
  1               5                  10
```

CASEIN FROM KOREAN CATTLE

FIELD OF THE INVENTION

The present invention is generally directed to a casein having a novel amino acid sequence and process for the preparation thereof. In particular, the present invention relates to a casein having a novel amino acid sequence which solubilizes minerals to promote an absorption thereof in the alimentary tract in animals, and process for the preparation thereof.

DESCRIPTION OF THE PRIOR ART

In general, minerals should be kept in a soluble state to be absorbed into animals. However, as contents moves through the small intestine in animals, a pH thereof shifts from a neutral to an alkaline state. In accordance with the change of pH in the small intestine, a large portion of minerals becomes insoluble to cause a precipitation. Concerning a calcium absorption, as a calcium moves through the small intestine, a portion of soluble calcium decreases in inverse proportion to an increase of pH therein. It is known that when a casein is supplied into animals together with calcium, a soluble calcium significantly increases in the small intestine in animals compared with a supply of calcium alone.

While an active transport prevails in the upper small intestinal tract in the calcium absorption, a passive transport is dominant in the lower small intestinal tract based on a concentration equilibrium. It is also suggested that vitamin D and lactose further promote the calcium absorption in animals. Although an absorption rate of calcium reveals high in the upper part of the small intestine, i.e., the duodena in animals, the retention time of contents is so short that the whole amount of calcium absorption therein is relatively low. In contrast, due to the long retention time of a diet, the ileum located in the lower part of the small intestine is an important part at which a large portion of calcium is absorbed. In fact, 62 or 88% of calcium is absorbed in the ileum in rats; and the calcium absorption in a human body excised with the ileum decreases greatly. It is accordingly understood that a casein phosphopeptide (hereinafter, referred to as "CPP") plays an important role in a calcium absorption (Sato et al., "Casein phosphopeptide contributing to an absorption of Ca in dairy product," Chemistry and Biology, Vol. 23, No. 7, p. 418 (1985)).

An obesity is one of the most dangerous hazard to threaten the health of modern people, which is largely due to high calory foods and beverages insufficient in vitamins and minerals. It is known that such unbalanced foodstuffs are responsible for diseases of adult people such as an osteoporosis. In order to prepare balanced foodstuffs, many researchers have tried to add one or more insufficient minerals to the foodstuffs. However, almost those attempts have been found unsuccessful because an addition of one mineral results in an absorption inhibition or decrease of other minerals in animals. Accordingly, it is desired to increase a mineral absorption rate in animals without adding minerals to foodstuffs. In the view of this respect, a casein has been considered as an important material.

A casein is one kind of protein contained in bovine or human milk, and α, β and γ types have been reported. In particular, β-casein have $A^1, A^2, A^3$, B, C, D and E variants whose primary structures have been already suggested (W. N. Eigel, et al., Nomenclature of Proteins of Cow's milk (5th Revision), J. Dairy Sci. Vol. 67, No. 8, pp. 1607–8 (1984)). The amino acid sequence of $A^2$ variant of representative β-casein is as follows (SEQ ID NO: 2):

Arg-Glu-Leu-Glu-Glu-Leu-Asn-Val-Pro-Gly-
 5                                      10

Glu-Ile-Val-Glu-Ser-Leu-Ser-Ser-Ser-Glu-
 15                                     20

Glu-Ser-Ile-Thr-Arg-Ile-Asn-Lys-Lys-Ile-
 25                                     30

Glu-Lys-Phe-Gln-Ser-Glu-Glu-Gln-Gin-Gln-
 35                                     40

Thr-Glu-Asp-Glu-Leu-Gln-Asp-Lys-Ile-His-
 45                                     50

Pro-Phe-Ala-Gln-Thr-Gln-Ser-Leu-Val-Tyr-
 55                                     60

Pro-Phe-Pro-Gly-Pro-Ile-Pro-Asp-Ser-Leu-
 65                                     70

Pro-Gln-Asn-Ile-Pro-Pro-Leu-Thr-Gln-Thr-
 75                                     80

Pro-Val-Val-Val-Pro-Pro-Phe-Leu-Gln-Pro-
 85                                     90

Glu-Val-Met-Gly-Val-Ser-Lys-Val-Lys-Glu-
 95                                     100

Ala-Met-Ala-Pro-Lys-His-Lys-Glu-Met-Pro-
 105                                    110

Phe-Pro-Lys-Tyr-Pro-Val-Gln-Pro-Phe-Thr-
 115                                    120

Glu-Ser-Gln-Ser-Leu-Thr-Leu-Thr-Asp-Val-
 125                                    130

Glu-Asp-Leu-His-Leu-Pro-Pro-Leu-Leu-Leu-
 135                                    140

Gln-Ser-Trp-Met-His-Gln-Pro-His-Gln-Pro-
 145                                    150

Leu-Pro-Pro-Thr-Val-Met-Phe-Pro-Pro-Gln-
 155                                    160

Ser-Val-Leu-Ser-Leu-Ser-Gln-Ser-Lys-Val-
 165                                    170

Leu-Pro-Val-Pro-Glu-Lys-Ala-Val-Pro-Tyr-
 175                                    180

Pro-Gln-Arg-Asp-Met-Pro-Ile-Gln-Ala-Phe-
 185                                    190

Leu-Leu-Tyr-Gln-Gln-Pro-Val-Leu-Gly-Pro-
 195                                    200

Val-Arg-Gly-Pro-Phe-Pro-Ile-Ile-Val.
 205

In addition, among the variants of casein, $A^1$ variant has amino acid sequence, wherein the 67th Pro is substituted by His, and $A^3$ variant has amino acid sequence, wherein the 106th His is substituted by Gln, in comparision with $A^2$ variant.

A casein or CPP has been widely used in various purposes. By using its mineral solubilizing effect, Japanese Laid-Open patent Publication No. Hei 5-336894 discloses health foodstuffs enriched with CPP. Japanese Laid-Open Patent Publication No. Hei 5-176712 also teaches foodstuffs containing CPP and alkaline phosphatase. Further, Japanese Laid-Open Patent Publication No. Hei 4-299942 illustrates an improved feed for the fowls containing CPP.

Both PCT Publication No. WO 94/00146 and U.S. Pat. No. 5,015,628 have suggested an oral composition comprising CPP to prevent or relieve dental calculuses or a dental hypersensitivity. In addition, Japanese Laid-Open Patent Publication No. Hei 1-269499 teaches a process for producing a skin or a hair care products containing CPP.

The disclosure of all references cited herein is incorporated by reference.

SUMMARY OF THE INVENTION

Previously, the present inventors have endeavored to enhance the intestinal mineral absorption in connection with CPP and disclosed, in Korean Patent Application No. 1995-6259, a novel CPP which differs its structure and the amino acid sequence from those of a conventional CPP.

Further, the present inventors have tried to find out the structure of a novel casein, finally found the full amino acid sequence of a novel casein, and its potency of solubilizing minerals in the alimentary tract in animals.

The inventive casein of a novel amino acid sequence referred herein as SEQ. ID NO: 1 having 209 amino acids, wherein the 25th Arg is substituted by Cys, the 88th Leu is substituted by Ile, the 117th Gln is substituted by Glu, the 175th Glu is substituted by Gln, and the 195th Gln is substituted by Glu, in comparision with the conventional $A^2$ variant of β-casein. In the corresponding DNA sequence, the 22nd Ser can be phosphorylated. It is known that phosphoserine has an effect to solubilizing minerals such as calcium and iron.

It is therefore an object of the invention is to provide a novel casein (hereinafter, referred to as "the inventive casein") having an amino acid sequence of SEQ. ID NO: 1.

Another object of the invention is to provide the respective processes for producing the inventive casein.

Still another object of the invention is to provide a process for selecting a bovine individual which produces milk containing the inventive casein.

Still another object of the invention is to provide a bovine individual which can secrete a large amount of the inventive casein.

BRIEF DESCRIPTION OF THE DRAWINGS

Other object, features and advantages of the invention will become apparent from the following description of the preferred embodiment taken in conjunction with the accompanying drawings in which.

DETAILED DESCRIPTION OF THE PREFERRED EMBODIMENT

Proteins and minerals generally tend to be bound to each other, and the types and strength of such couplings are largely dependent upon their higher structures, i.e., secondary or tertiary structure (Naito, "The Mechanism of Enhancement in Intestinal Calcium Absorption with Phosphopeptides Derived during Casein Digestion," J. of Japanese Nutr. and Food, Vol. 39, No. 6, pp. 433, 436 (1986)). Due to differences of the amino acid sequence and primary structure, the inventive casein containing same show an improved ability to solubilize minerals including calcium in the small intestine; and therefore, it naturally entails an enhancement of mineral absorption in animals.

In accordance with the present invention, there is provided a novel casein having a novel amino acid sequence of SEQ. ID NO: 1.

As already suggested, a phosphoserine (15th), three successive phosphoserines (17th to 19th) and two glutamic acid residues (20th and 21st) form a strong negative charge area, which provide an active site with respect to a calcium (Naito, supra). That is, caseins form a dimer via 25th Cys residue from the N-terminal, or CPPs which are formed from digestion of casein, form a dimer. It is understood that a dimer of the inventive casein protects a stability of the above-mentioned active area of a phosphoserine, three successive phosphoserines and two glutamic acids; and, therefore, the inventive casein has an improved ability to solubilize minerals.

In another aspect of the invention, there is provided a process for producing the inventive casein having the amino acid sequence of SEQ. ID. NO: 1 comprising the steps of: selecting a bovine individual which produces milk containing the inventive casein; hybridizing said bovine with another bovine breed which secretes a lot of milk to obtain Fl descendants; selecting a cow which produces milk containing the inventive casein among said Fl descendants; extracting milk containing the inventive casein from said cow, and adding an acid or a rennet to said milk to precipitate; and recovering the precipitated casein.

Figure 1:
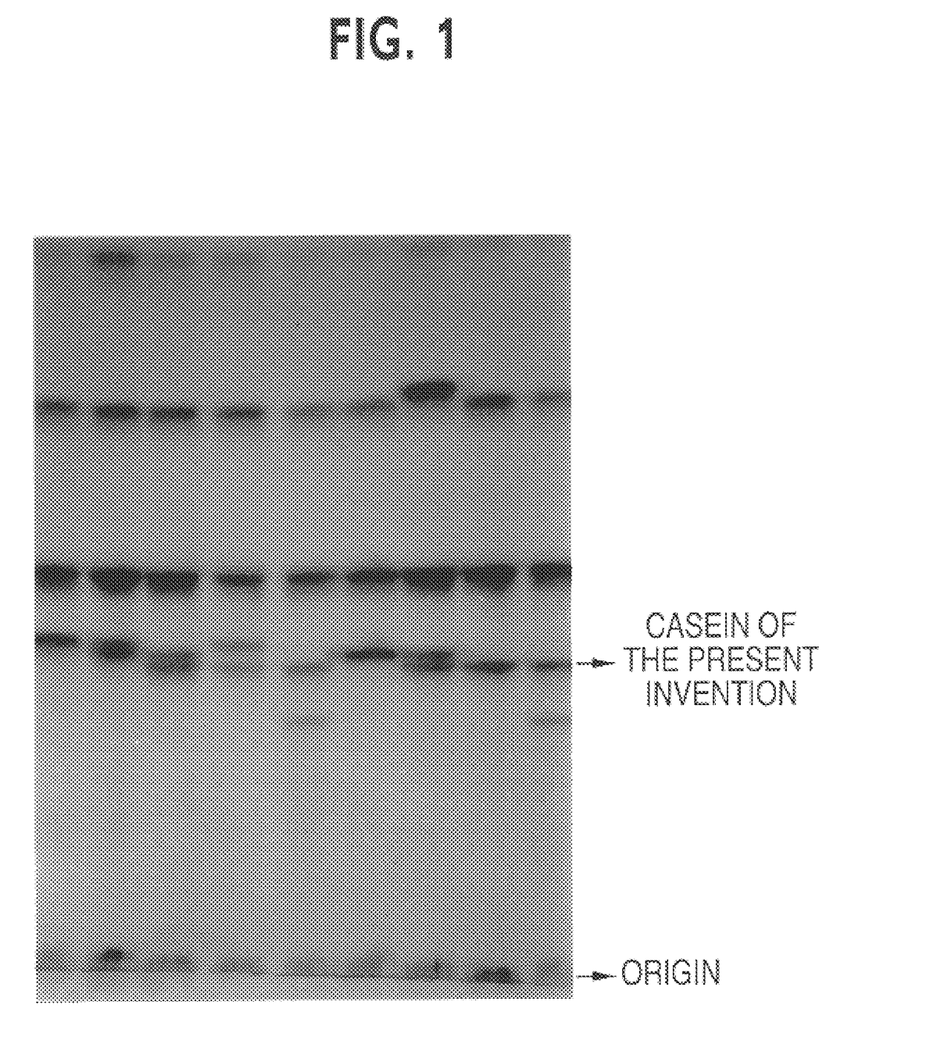
FIG. 1 is a photograph of electrophoresis with respect to the inventive casein in accordance with the present invention.

In the process, the selection of milk containing the inventive casein is carried out by an electrophoresis which shows a characteristic band in FIG. 1. Representative examples of acids which can preferably be added to milk include: a hydrochloric acid and lactic acid. The precipitated casein can be recovered by chromatographys. It is preferred that an anion exchange chromatography and then a cation exchange chromatography are conducted successively.

The inventive casein can be identified by the peculiar band as shown in FIG. 1 as a result of an electrophoresis.

Since the inventive casein is produced from milk containing the inventive casein, it is necessary to produce milk containing the inventive casein in a large scale. For this purpose, there is provided a process for producing milk containing the inventive casein comprising the steps of: selecting a bovine individual which produces milk containing the inventive casein, hybridizing said bovine with another bovine breed which secretes a lot of milk to obtain Fl descendants, selecting a cow which produces milk containing the inventive casein among said Fl descendants, and extracting milk containing the inventive casein from said cow.

In still other aspect of the present invention, there is provided a process for selecting a bovine individual which produces milk containing the inventive casein, comprising the steps of: extracting a material containing DNA from a bovine individual; separating a DNA from the extracted material; and analyzing the amino acid sequence of said DNA.

In order to select a bovine individual of the inventive casein, a material containing DNA extracted from a cattle such as blood, tissue and semen is analyzed for a DNA sequence to compare with the sequence of SEQ. ID NO: 1 referred herein. As an alternative, an electrophoresis may conducted for milk to find a unique band as shown in FIG. 1. The selected bovine individual of the inventive casein is then copulated with another bovine species which produces much milk, for example, Holstein species. It has been found that some descendants (Fl) obtained therefrom have a genetic information of the inventive casein which produce milk containing the desired inventive casein. Thus selected improved bovine individual produces milk containing the inventive casein with a high productivity, which is most suitable for the mass production of the inventive casein in accordance with the present invention.

In contrast, in the case of a bovine individual which cannot produce milk(bull, abortive cow, calf etc.), since it is impossible to separate milk, the casein of these animals can be identified by extracting blood, semen or tissue containing DNA, separating DNA therefrom, and analyzing the amino acid sequence of DNA. Also, since a casein having 25th Cys in the amino acid sequence of SEQ. ID NO: 1 should be fall within the secope of the present invention, we can select bovine individual which can produce the inventive casein detecting 25th Cys in the amino acid sequence.

It is possible to find whether the amino acid sequence of DNA sample corresponds to that of the present invention by sequencing DNA sample and comparing that with amino acid sequence of the present invention. Also, it is possible to find whether the amino acid sequence of DNA sample corresponds to that of the present invention by adding NIS I incision enzyme to CPP. In this method, if 25th amino acid of CPP is catabolized, it is included in a casein of the present invention.

The present invention further provides a bovine individual which can secrete a large amount of the inventive casein, obtained by selecting a bovine individual which produces milk containing a new casein and hybridizing said bovine with another bovine breed which secretes a lot of milk.

The following Examples are given for the purpose of illustration only and are not intended to limit the scope of the invention.

EXAMPLE 1

Preparation of a Novel Casein in Accordance with the Present Invention (hereinafter, referred to "a new casein")

Various bovine milk were centrifugated at 5,000 RPM for 20 minutes, followed by removing the supernant fatty layer. The resultant was added to starch gel (Connought Medical Research Lab.); and an electrophoresis was carried out at 150 volts for 12 hours by using a buffer (pH: 1.5) consisting of 850 ml of deionized water, 100 ml of acetic acid and 50 ml of formic acid. The gel was stained by 10% of nigrosin solution for 30 minutes and then destained by adding 50% of methanol for 5 hours. The resulting electrophoresis photograph is shown in FIG. 1, wherein the inventive casein is identified by its specific band.

Figure 2:
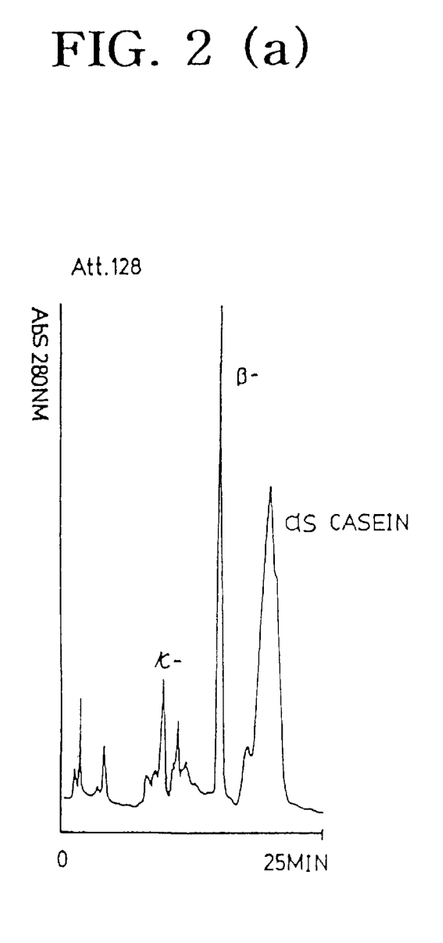
FIG. 2(a) is a chromatogram showing the inventive casein peak after passing the casein through a cation exchange column.
FIG. 2(b) is a chromatogram showing the inventive casein peak after passing the casein of FIG. 2(a) through the first anion exchange column.
FIG. 2(c) is a chromatogram showing the inventive casein peak after passing the casein of FIG. 2(b) through the second anion exchange column.

Bovine milk which was found to contain the above casein was then centrifugated, followed by removing fatty layer of the supernant. The casein protein was precipitated by adding a hydrochloric acid and subjected to a free-drying. By passing 10 g of the casein through a cation exchange column (Model: Mono Q 5/5 manufactured by Pharmarcia Co.) using 2 mM of imidazole-HCl buffer (pH 7.0), a purified casein of the present invention was obtained. The chromatogram is shown in FIG. 2(a).

The resulting new casein was subjected to a first anion exchange column (Model: Mono S 5/5 manufactured by Pharmarcia Co.) by using 50 mM of sodium acetate buffer (pH 5.0) to give the inventive casein protein. The result is shown in FIG. 2(b). A second anion exchange column was carried out for the casein to yield 1.5 g of the inventive casein protein in a pure form. The chromatogram is shown in FIG. 2(c).

EXAMPLE 2

Analysis of Chemical Property of the Inventive Casein

To the purified casein obtained in Example 1, 6N trypsin (manufactured by Sigma Co.) was added to hydrolyze. After the completion of the reaction, resulting hydrolyzate was subjected to HPLC (RP-column manufactured by Merk) to yield a pure CPP.

The purified CPP was subjected to a protein sequencer (Applied-Bio System Co.) to provide the amino acid sequence, which gives the amino acid sequence of the inventive casein.

EXAMPLE 3

Mass Production of the Inventive Casein by Animal Secretion

For a mass production of the inventive casein by way of an animal secretion, a Korean Bull ($A^1H$ type) having the genetic information of the inventive casein identified by the process as shown in following Example 4 was copulated with five Holstein cows (two of $A^1A^1$, two of $A^1A^2$ and one $A^2A^2$ types) to give birth to two male calves and three female calves. The DNA analysis for the three female calves were conducted to find one female calf ($A^1H$) and one male calf ($A^2H$) of the inventive casein as heterozygote.

Thus obtained female calf (Fl) having the genetic information of the inventive casein ($A^1H$) was raised and conceived for 28 months from its birth date. The milk produced therefrom was found to contain the inventive casein with an yield of approximately 4.5 Kg per day. That is, the milk productivity of the cow (Fl) revealed 3 times higher than the prior Korean Cattle of the inventive casein.

As a result of studying the heredity over 3 generations for 23 families having the genetic information of the inventive casein, it is found that the genetic information of the inventive casein can be coinherited.

EXAMPLE 4

DNA Analysis for the Inventive Casein 20 ml of blood was extracted from a Korean Native Cattle secreting the inventive casein and then a DNA was purified according to a conventional method proposed by Sambrook (Sambrook et al., Molecular Cloning, Cold Spring Harbor Lab. Press, (1989)).

To amplify a DNA fragment containing the substituted amino acid in the inventive casein, a primer was-prepared by referring to a process suggested by Bosing (Bosing et al., Complete Nucleotide Sequence of the Bovine Beta-Casein Gene, Aust, J. Biol. Sci., Vol. 41, p. 527 (1988)). The DNA sequence of the prepared primer is as follows:

Primer 5'-CAACAGCCTTATTCAGAAGAGTGG (SEQ ID NO: 3)
3'-CAGTGGGATGACAGAAAGTAGTCGTATAGG (SEQ ID NO: 4)

0.5 μg of the purified DNA, 0.5 μl of each primers (100 pmol/μl), 5 μl of dNTP, 5 μl of 10×buffer, 1 μl of Taq polymerase (1 unit) and 33 μl of distilled water were mixed. The DNA was denatured by heating the mixture at a temperature of 94° C. for 5 minutes. Thereafter, PCR (polymerase chain reaction) cycles were repeated 30 times for 60 seconds at 94° C., 60 seconds at 57° C. and 60 seconds at 72° C. After completing the PCR reactions, 5 minutes of extension time was provided to form double standard helices from the amplified DNA fragments.

The amplified DNA was purified by an electrophoresis using 2% of agarose (Gibco Co.) and then the DNA sequence was analyzed by Automatic DNA sequencer (Applied Bio System Co.). The analyzed DNA sequence for the part of the CPP having the substituted amino acid residues is as follows (SEQ ID NO: 5):

```
        intron 4                              exon 5
TTTTTTAAAGCTAGACCTGATTTTATTTTTATTTTTCCAAAG   GAA TCT ATT
                                              Glu Ser Ile intron 5
   Nis I incision position
   |
ACA TGC ATC AAT AAG GTAAAACCCCTCATATTTAAATGTACATTTTTTAA
```

Thr Cys Ile Asn Lys (SEQ ID NO: 6)
ATTTCATGTTTGATTTTTATAAACAGCATTTATTTA
TGTATTTTTTTTTAACCAG
exon 6
AAA ATT GAG AAG TTT CAG AGT GAG GAA CAG CAG CAA
Lys Ile Glu Lys Phe Gln Ser Glu Glu Gln Gln Gln (SEQ ID NO: 7)

Figure 3:
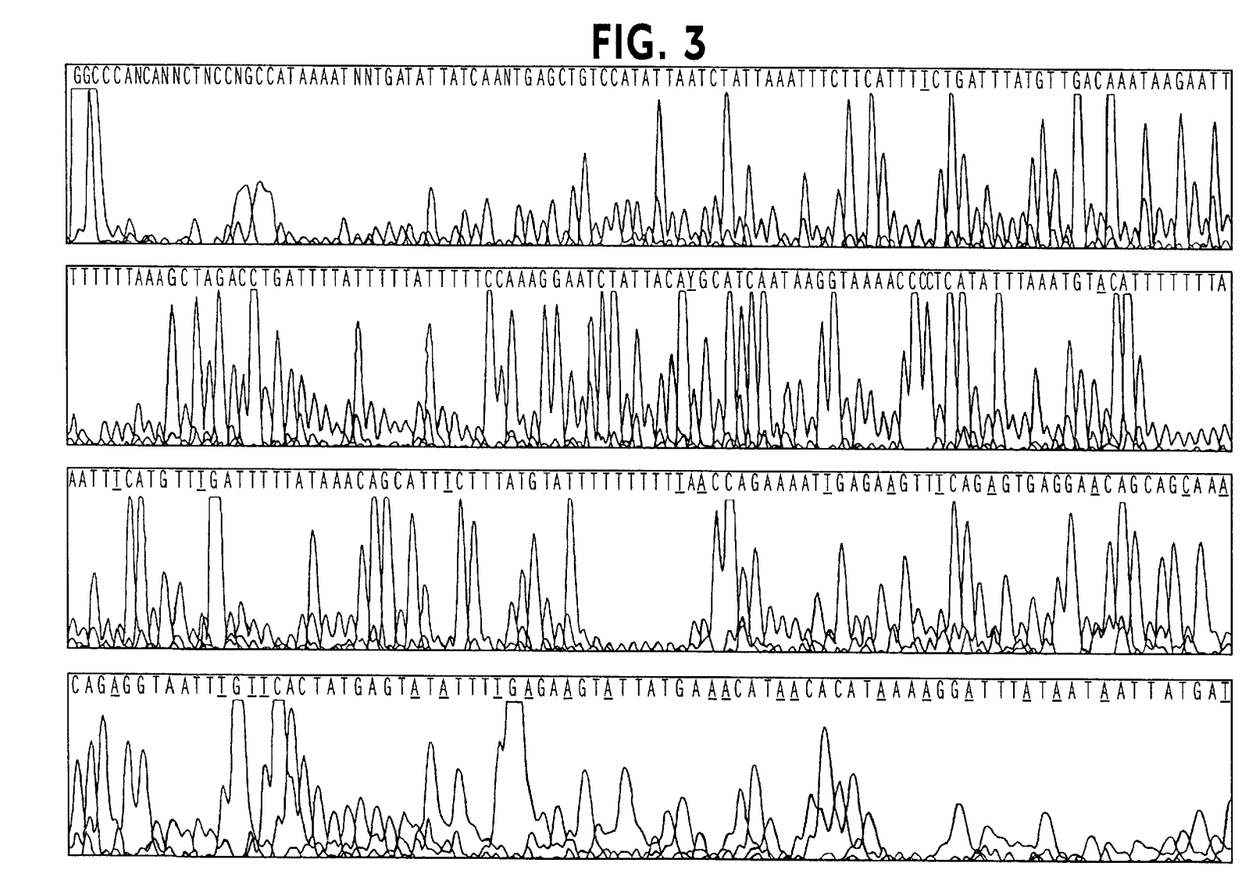
FIG. 3 is a diagram showing a part of the DNA sequence of the inventive casein in accordance with the present invention.

The diagram for the DNA sequencing is shown in FIG. 3.

As shown above, the 13rd base in exon 5 is replaced from cytosine to thymine evidencing the replacement of amino acid from Arg to Cys in the CPP in the present invention.

EXAMPLE 5

Efficacy Test for Calcium Solubilizing Effect In Vivo

Forty Wister Rats weighing about 120 g on an average were supplied with a controlled diet consisting of 24 wt % of crude proteins, 5 wt % of crude fats 60 wt % of starches, 5 wt % of crude fibers, 5 wt % of minerals and 1 wt % of vitamins for a week and then starved for 24 hours. The rats were divided into 2 groups, each group including 10 rats.

Rats of the first group were supplied with a controlled diet including 10 wt % of the inventive casein for 1.5 hours.

Rats of the second group were supplied with a controlled diet including 10 wt % of a conventional new casein for 1.5 hours.

All rats were allowed to freely have the controlled diets as much as they can. One hour after the completion of the above feeding, all rats were anesthetized, and the small intestines were excised therefrom. The small intestines were washed with a saline solution and then divided into two parts, i.e., the upper part and the lower part.

Thereafter, the contents in the small intestine were isolated, homogenized and centrifugated. A calcium in the supernant was measured three times by an atomic absorption spectrometer (Perkin Elmer Co.). The results are shown in Table 1 below.

TABLE 1

Calcium concentration in the small intestine in case of casein feed

| | 1st Group | 2nd Group | Improvement (%) |
|---|---|---|---|
| Upper part | 16.26 ± 1.8 | 15.49 ± 1.7 | 4.9 |
| Lower part | 42.23 ± 2.5 | 35.11 ± 2.3 | 20.2 |

*mean ppm ± standard deviation

As shown in Table 1 above, concentration in the small intestine of soluble calcium in the first group rats supplied with the inventive casein showed 16.25 in upper part, 42.25 ppm (average) in lower part, and that in the second group rats supplied with the prior casein showed 15.49 in upper part, 35.11 ppm (average) in lower part. In particular, lower part of the small intestine the concentration of soluble calcium in the 1st group amounts to 20.2% improvement over that in 2nd group.

Accordingly, it appears that the inventive casein has an unexpectedly surprising calcium solubilizing effect in vivo over the conventional casein and CPP.

Industrial Availability

Accordingly, the inventive casein can be used as a composition for health food or beverage comprising the inventive casein and edible carriers. Examples of the composition include: milk, powdered milk for baby or patients, yoghourts (liquid, creamy or frozen type), cheese, weaning diet, confectionery, breads ice creams, bean curds, candy, frozen sweets, oil-and-honey pastry, chocolate, caramel, natural or artificial juices, boiled fish pastes, thirsty quenches (isotonic sports drinks), powdered tea, mayonnaise, dressings and the like.

Particularly, the inventive casein in accordance with the present invention is preferably added to foodstuffs excluding lactose for infants or adults who are allergic thereto.

Still another aspect of this invention, the inventive casein can be used as a medical composition comprising the inventive casein in an effective amount of preventing, treating or relieving a disease caused by a mineral malnutrition in animals, and a pharmaceutically acceptable carrier. The disease caused by a mineral malnutrition such as osteoporosis or anemia can be treated or relieved by orally administering the medical composition above.

Further, the inventive casein can be used as an oral composition comprising the inventive casein and a pharmaceutically acceptable carrier. The oral composition include: aqueous, aqueous-alcohol or alcohol solution or dispersion of casein or the CPP in the form of a mouth wash, dentifrice, toothpaste, toothpowder, gel, lozenge, tablet, chewing gum, or any other suitable form of oral composition.

The inventive casein containing same may be added to a composition, i.e., skin or hair care products, or a feed composition in an effective amount of enhancing a mineral absorption in animals, and edible carrier.

Since the inventive casein has a higher mineral solubilizing effect, it is of course used for every purposes noted above, rendering products including same more effective.

While the invention has been described with reference to a preferred embodiment, it should be apparent to those skilled in the art that many changes and modifications may be made without departing from the spirit and scope of the invention as defined in the claims.

SEQUENCE LISTING

What is claimed is:

1. A casein having the amino acid sequence of SEQ ID NO: 1.

* * * * *